US012059259B2

(12) United States Patent
Meng

(10) Patent No.: US 12,059,259 B2
(45) Date of Patent: Aug. 13, 2024

(54) METHOD AND APPARATUS FOR PROCESSING AN ELECTROCARDIOGRAM SIGNAL AND ELECTRONIC DEVICE

(71) Applicant: BOE Technology Group Co., Ltd., Beijing (CN)

(72) Inventor: Guifang Meng, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 732 days.

(21) Appl. No.: 17/289,082

(22) PCT Filed: Sep. 25, 2020

(86) PCT No.: PCT/CN2020/117707
§ 371 (c)(1),
(2) Date: Apr. 27, 2021

(87) PCT Pub. No.: WO2021/103796
PCT Pub. Date: Jun. 3, 2021

(65) Prior Publication Data
US 2022/0304610 A1  Sep. 29, 2022

(30) Foreign Application Priority Data

Nov. 29, 2019  (CN) .......................... 201911211864.7

(51) Int. Cl.
A61B 5/00  (2006.01)
A61B 5/024  (2006.01)
A61B 5/318  (2021.01)

(52) U.S. Cl.
CPC .............. A61B 5/318 (2021.01); A61B 5/024 (2013.01); A61B 5/7203 (2013.01)

(58) Field of Classification Search
CPC ....... A61B 5/318; A61B 5/024; A61B 5/7203; A61B 5/02405; A61B 5/361; A61B 5/364;
(Continued)

(56) References Cited

U.S. PATENT DOCUMENTS 8,475,387 B2 * 7/2013 Derchak .............. A61B 5/0205
600/534
10,213,145 B1 * 2/2019 McNair ................ A61B 5/0245
(Continued)

FOREIGN PATENT DOCUMENTS

CN   102284138 A   12/2011
CN   105496402 A   4/2016
(Continued)

OTHER PUBLICATIONS

Office Action dated Jan. 28, 2021, issued in counterpart CN application No. 201911211864.7, with English translation. (23 pages).
(Continued)

Primary Examiner — May A Abouelela
(74) Attorney, Agent, or Firm — WHDA, LLP

(57) ABSTRACT

The present disclosure provides a method and apparatus for processing an electrocardiogram signal and an electronic device. The method includes: obtaining an electrocardiogram signal containing a plurality of selected waves; determining an interval sequence for the plurality of selected waves; converting the interval sequence into a symbol value sequence, based on symbolic dynamics; determining a Shannon entropy of the symbol value sequence; and classifying the electrocardiogram signal, based on a value of the Shannon entropy.

16 Claims, 8 Drawing Sheets

Figure 1:
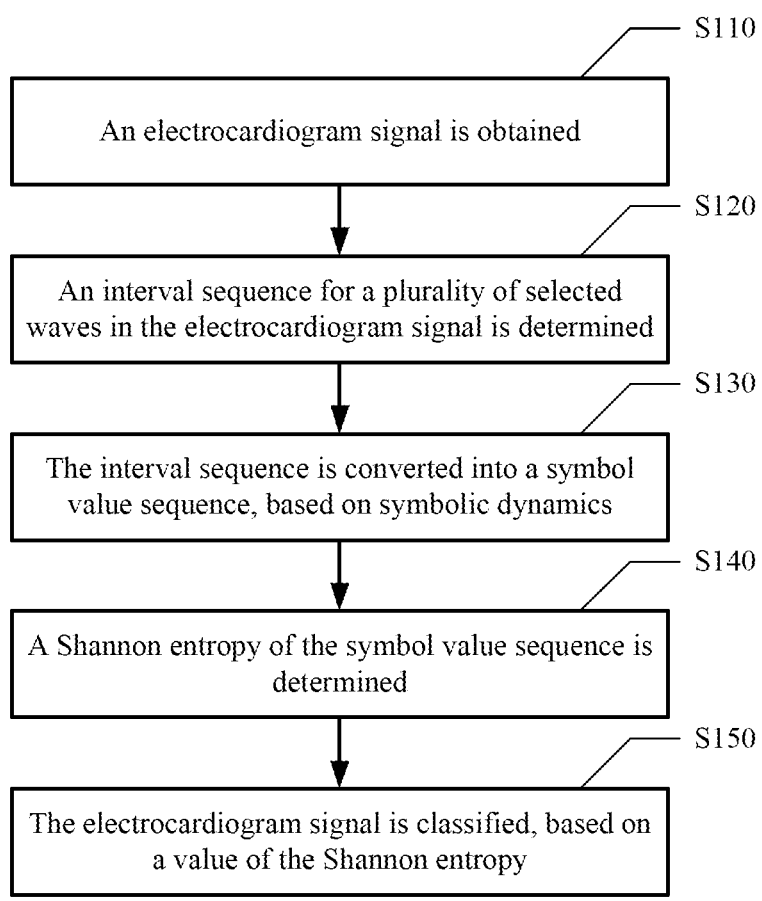

(58) Field of Classification Search
CPC ....... A61B 5/7264; A61B 5/352; A61B 5/316; A61B 5/7235; A61B 5/7267; G06F 2218/10; G06F 2218/12
See application file for complete search history.

(56) References Cited

U.S. PATENT DOCUMENTS

| | | | | |
|---|---|---|---|---|
| 11,918,352 | B2* | 3/2024 | MacIntyre | A61B 5/4845 |
| 2003/0055348 | A1* | 3/2003 | Chazal | A61B 5/4818 |
| | | | | 600/509 |
| 2009/0112110 | A1* | 4/2009 | Zhang | A61B 5/7203 |
| | | | | 600/518 |
| 2012/0016249 | A1 | 1/2012 | Lian et al. | |
| 2012/0232414 | A1* | 9/2012 | Mollicone | A61B 5/024 |
| | | | | 600/508 |
| 2013/0190638 | A1* | 7/2013 | Chon | A61B 5/332 |
| | | | | 600/521 |
| 2014/0276156 | A1* | 9/2014 | Zhang | A61B 5/353 |
| | | | | 600/509 |
| 2015/0313553 | A1* | 11/2015 | Chon | A61B 5/363 |
| | | | | 600/508 |
| 2016/0063207 | A1* | 3/2016 | Schmidt | G16H 50/30 |
| | | | | 705/2 |
| 2017/0224238 | A1 | 8/2017 | Arunachalam et al. | |
| 2018/0110432 | A1* | 4/2018 | Nam | A61B 5/349 |
| 2018/0184915 | A1* | 7/2018 | Darbari | A61B 7/04 |
| 2018/0199893 | A1* | 7/2018 | Hubner | G16H 50/20 |
| 2019/0269328 | A1* | 9/2019 | Porges | A61B 5/11 |
| 2020/0121255 | A1* | 4/2020 | Tian | A61B 5/7221 |
| 2020/0375480 | A1 | 12/2020 | Costa et al. | |
| 2021/0282692 | A1* | 9/2021 | Yaniv | A61B 5/7267 |
| 2023/0397829 | A1* | 12/2023 | King, IV | A61B 5/0205 |
| 2023/0397892 | A1* | 12/2023 | da Silva | A61B 5/7275 |
| 2023/0398356 | A1* | 12/2023 | Poltorak | A61B 5/369 |
| 2023/0402186 | A1* | 12/2023 | Kim | A61B 5/7264 |

FOREIGN PATENT DOCUMENTS

| | | |
|---|---|---|
| CN | 109452938 A | 3/2019 |
| CN | 109480819 A | 3/2019 |
| CN | 110363177 A | 10/2019 |
| CN | 110840443 A | 2/2020 |
| WO | 2018/175939 A1 | 9/2018 |

OTHER PUBLICATIONS

Office Action dated Jul. 8, 2021, issued in counterpart CN application No. 201911211864.7, with English translation. (15 pages).

International Search Report dated Jan. 4, 2021, issued in counterpart International application No. PCT/CN2020/117707, with English translation. (7 pages).

Written Opinion dated Jan. 4, 2021, issued in counterpart International application No. PCT/CN2020/117707. (4 pages).

Mu, Yuanhui, "ECG Arrhythmia Feature Extraction and Analysis by Multi-scale Time-frequency Method", Chinese Master's Theses Full-Text Database, Medicine & Health Sciences, 2016, No. 3, pp. 1-57, cited in ISR dated Jan. 4, 2021, with English translation. (46 pages).

Chunhua, Bian et al, "Entropy Analysis Method of Short-Term Heart Rate Variability Symbol Sequence", Science in China Press, vol. 54, No. 3, 2019, pp. 340-344, cited in ISR dated Jan. 4, 2021, with English translation. (14 pages).

Parlitz, U. et al., "Classifying Cardiac Biosignals using Ordinal Pattern Statistics and Symbolic Dynamics", Computers in Biology and Medicine, 2012, vol. 42, No. 3, pp. 319-327, cited in ISR dated Jan. 4, 2021. (9 pages).

Zhou, Xiaolin et al. "Automatic online detection of atrial fibrillation based on symbolic dynamics and Shannon entropy", BioMedical Engineering, 2014, vol. 13, No. 18, pp. 1-18, cited in CN Office Action dated Jan. 28, 2021. (18 pages).

Zhang, Yue et al., "Research on Algorithm for Detecting Atrial Fibrillation Using RR Intervals", ICALIP2018, 2018, pp. 205-209, cited in CN Office Action dated Jan. 28, 2021. (5 pages).

* cited by examiner

METHOD AND APPARATUS FOR PROCESSING AN ELECTROCARDIOGRAM SIGNAL AND ELECTRONIC DEVICE

CROSS-REFERENCE TO RELATED APPLICATION(S)

This application is a Section 371 National Stage Application of International Application No. PCT/CN2020/117707, which claims priority to the Chinese Patent Application No. 201911211864.7, filed on Nov. 29, 2019, which is incorporated herein by reference in its entirety.

TECHNICAL FIELD

The present disclosure relates to a field of computer technology, and more particularly, to a method and apparatus for processing an electrocardiogram signal and an electronic device.

BACKGROUND

An electrocardiogram (ECG) signal is a comprehensive reflection of electrical heart activities on a body surface. Accurate classification for an ECG signal may provide effective assistance for scenarios such as clinical monitoring and telemedicine. The ECG signal may be classified by training a classifier. In this manner, a large amount of sample data is prepared, feature construction is performed on the sample data, and the classifier is trained based on the feature of the sample data until an optimization goal is reached. However, this is complicated and less efficient.

SUMMARY

According to the embodiments of the present disclosure, a method and apparatus for processing an electrocardiogram signal and an electronic device are provided.

According to an aspect of the present disclosure, there is provided a method for processing an electrocardiogram signal, including: obtaining an electrocardiogram signal containing a plurality of selected waves; determining an interval sequence for the plurality of selected waves; converting the interval sequence into a symbol value sequence, based on symbolic dynamics; determining a Shannon entropy of the symbol value sequence; and classifying the electrocardiogram signal, based on a value of the Shannon entropy.

For example, the classifying the electrocardiogram signal, based on a value of the Shannon entropy includes: determining that the electrocardiogram signal belongs to a first predetermined category, in response to the value of the Shannon entropy being greater than a first predetermined threshold.

For example, the converting the interval sequence into a symbol value sequence, based on symbolic dynamics includes: obtaining an instantaneous heart rate sequence, by calculating an instantaneous heart rate for each time interval in the interval sequence; obtaining a plurality of encoded symbols, by performing a first encoding on each of a plurality of instantaneous heart rates in the instantaneous heart rate sequence respectively; determining a symbol sequence based on the plurality of encoded symbols; obtaining a plurality of symbol values, by performing a second encoding on each of the plurality of encoded symbols in the symbol sequence respectively; and determining a symbol value sequence, based on the plurality of symbol values.

For example, the obtaining a plurality of encoded symbols, by performing a first encoding on each of a plurality of instantaneous heart rates in the instantaneous heart rate sequence respectively includes: for any instantaneous heart rate of the instantaneous heart rates in the instantaneous heart rate sequence, classifying the any instantaneous heart rate, based on a value of the any instantaneous heart rate; setting a predetermined symbol as an encoded symbol for the any instantaneous heart rate, in response to the any instantaneous heart rate belonging to a first class; and setting a ratio of the any instantaneous heart rate to a first value as an encoded symbol for the any instantaneous heart rate, in response to the any instantaneous heart rate belonging to a second class.

For example, the obtaining a plurality of symbol values, by performing a second encoding on each of the plurality of encoded symbols in the symbol sequence respectively includes: for any encoded symbol of the encoded symbols in the symbol sequence, calculating a weighted sum of the any encoded symbol, a previous encoded symbol of the any encoded symbol and a subsequent encoded symbol of the any encoded symbol; and setting the weighted sum as a symbol value for the any encoded symbol.

For example, the determining a Shannon entropy of the symbol value sequence includes: presetting a plurality of symbol value sections; for any symbol value section of the plurality of symbol value sections, calculating a ratio of a number of symbol values in the symbol value sequence falling within the any symbol value section to a number of symbol values in the symbol value sequence, and setting the ratio as a distribution probability of the symbol value sequence with respect to the any symbol value section; and determining the Shannon entropy of the symbol value sequence, based on the distribution probability of the symbol value sequence with respect to each of the plurality of symbol value sections.

For example, the determining the Shannon entropy of the symbol value sequence, based on the distribution probability of the symbol value sequence with respect to each of the plurality of symbol value sections includes: calculating a distribution expectation of the symbol value sequence with respect to the plurality of symbol value sections, based on the distribution probability of the symbol value sequence with respect to each of the plurality of symbol value sections; determining a gain coefficient, based on the number of symbol values in the symbol value sequence and a number of the plurality of symbol value sections; and determining the Shannon entropy of the symbol value sequence, based on the distribution expectation and the gain coefficient.

For example, the method further includes: setting a sliding window, wherein a length of the sliding window is smaller than a length of the symbol value sequence; extracting a plurality of symbol value subsequences from the symbol value sequence, by sliding the sliding window from a head of the symbol value sequence to a tail of the symbol value sequence, wherein a step of the sliding window is one symbol value; for any symbol value subsequence of the plurality of symbol value subsequences, determining a Shannon entropy of the any symbol value subsequence, and adding one point to a score of each symbol value in the any symbol value subsequence, in response to the Shannon entropy of the any symbol value subsequence being greater than a first predetermined threshold; determining a total score of each symbol value in the symbol value sequence, after completing the sliding of the sliding window; and determining that a symbol value having a total score greater than a second predetermined threshold belongs to a first predetermined category.

For example, the determining an interval sequence for the plurality of selected waves includes: identifying a peak of each of the plurality of selected waves respectively; and determining the interval sequence, based on time intervals between every two adjacent peaks of the plurality of selected waves.

For example, the electrocardiogram signal contains M+1 selected waves. The determining the interval sequence, based on time intervals between every two adjacent peaks of the plurality of selected waves includes: determining an initial interval sequence containing M time intervals, based on time intervals between every two adjacent peaks of the M+1 selected waves; and obtaining an interval sequence containing N time intervals, by preprocessing the initial interval sequence, wherein M and N are both positive integers, and M is greater than or equal to N.

For example, the obtaining an interval sequence containing N time intervals, by preprocessing the initial interval sequence includes: determining a mean of the M time intervals; for any time interval of the M time intervals, determining whether the any time interval belongs to a second predetermined category or not, based on a difference between the any time interval and the mean; and deleting the any time interval and a subsequent time interval of the any time interval from the initial interval sequence, in response to determining that the any time interval belongs to the second predetermined category.

For example, the obtaining an interval sequence containing N time intervals, by preprocessing the initial interval sequence includes: determining a mean of the M time intervals; for any time interval of the M time intervals, obtaining a combined interval, by summing the any time interval and a subsequent time interval of the any time interval; determining whether the any time interval belongs to a second predetermined category or not, based on a difference between the combined interval and the mean; and combining the any time interval and the subsequent time interval of the any time interval as one time interval, in response to determining that the any time interval belongs to a second predetermined category.

For example, the obtaining an interval sequence containing N time intervals, by preprocessing the initial interval sequence includes at least one of: for any time interval of the M time intervals, deleting the any time interval and a subsequent time interval of the any time interval from the initial interval sequence, in response to a ratio of the any time interval to a previous time interval of the any time interval being greater than a second value, and a ratio of a subsequent time interval of the any time interval to the any time interval being greater than a third value; and for the any time interval, deleting the any time interval and a subsequent time interval of the any time interval from the initial interval sequence, in response to a ratio of the any time interval to a previous time interval of the any time interval being greater than a fourth value, and a ratio of a subsequent time interval of the any time interval to the any time interval being smaller than a fifth value, wherein the second value is smaller than the third value, and the fourth value is greater than the fifth value.

For example, the method further includes: removing baseline wander noise of the electrocardiogram signal, after obtaining the electrocardiogram signal.

For example, the electrocardiogram signal is a single-lead electrocardiogram signal.

According to another aspect of the present disclosure, there is provided an apparatus for processing an electrocardiogram signal, including: an obtaining module, a determining module, a converting module, an entropy calculating module, and an entropy calculating module. The obtaining module is configured to obtain an electrocardiogram signal containing a plurality of selected waves. The determining module is configured to determine an interval sequence for the plurality of selected waves. The converting module is configured to convert the interval sequence into a symbol value sequence, based on symbolic dynamics. The entropy calculating module is configured to determine a Shannon entropy of the symbol value sequence. The classifying module is configured to classify the electrocardiogram signal, based on a value of the Shannon entropy.

According to another aspect of the present disclosure, there is provided an electronic device, including: a memory and at least one processor. The memory is configured to store instructions. The at least one processor is configured to execute the instructions stored in the memory, in order to implement the method described above.

BRIEF DESCRIPTION OF THE ACCOMPANYING DRAWINGS

Figure 2A:
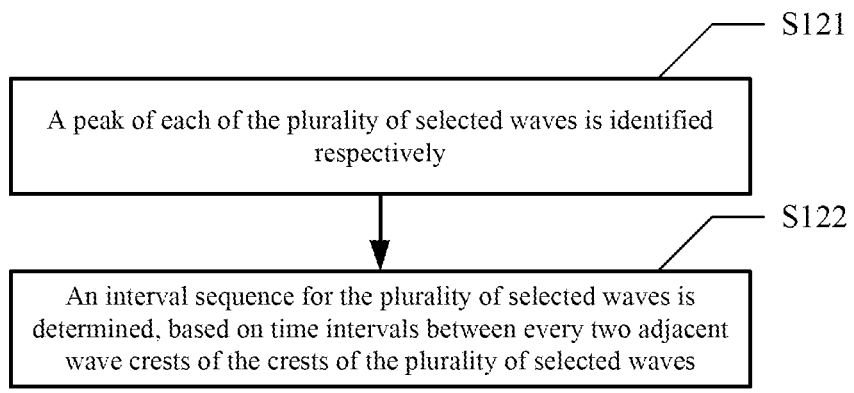
Figure 2B:
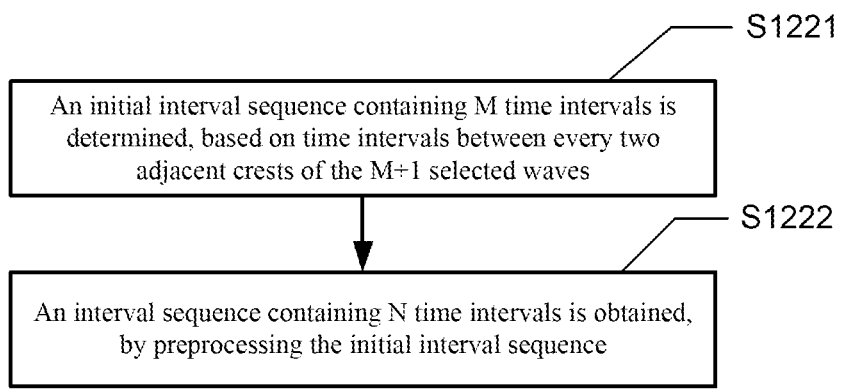
Figure 3:
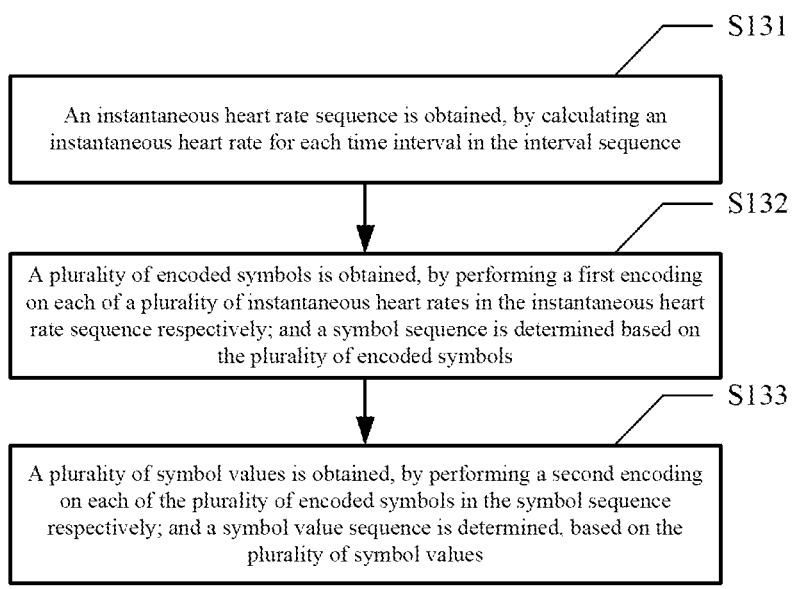
Figure 4:
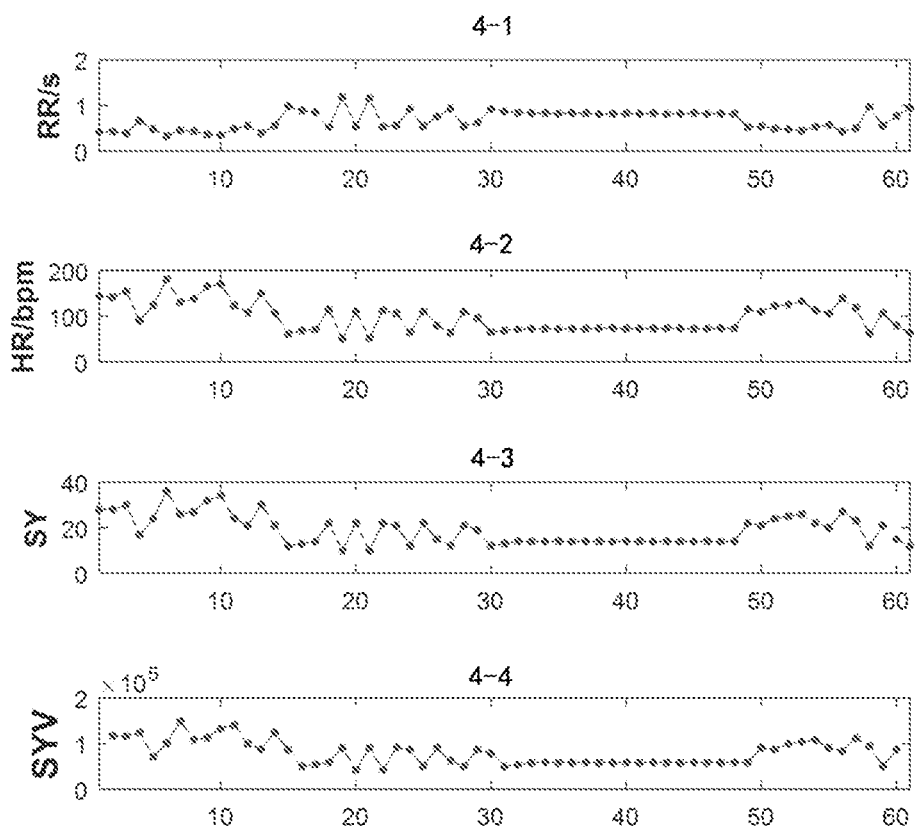
Figure 5:
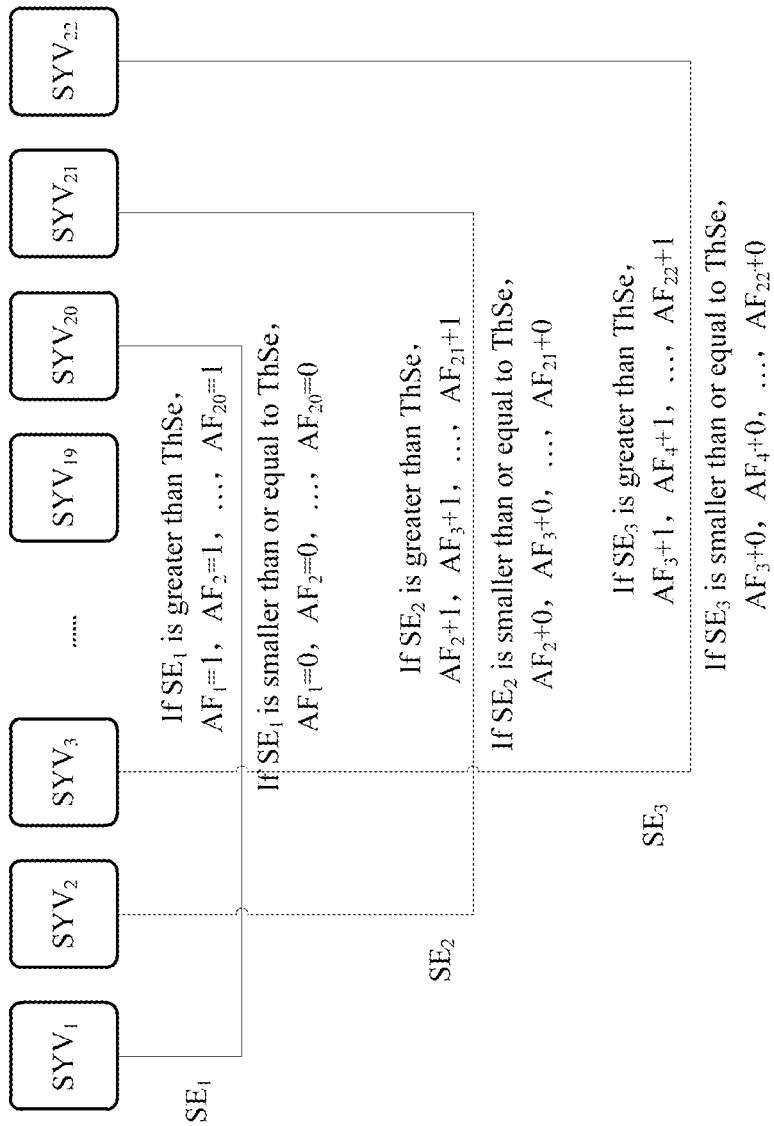
Figure 6A:
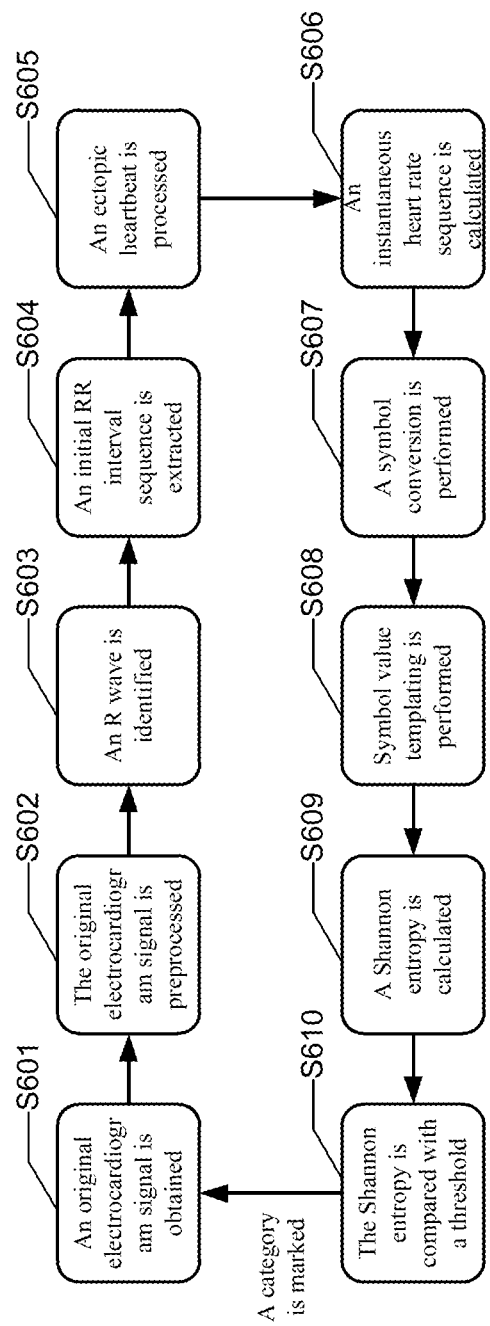
Figure 6B:
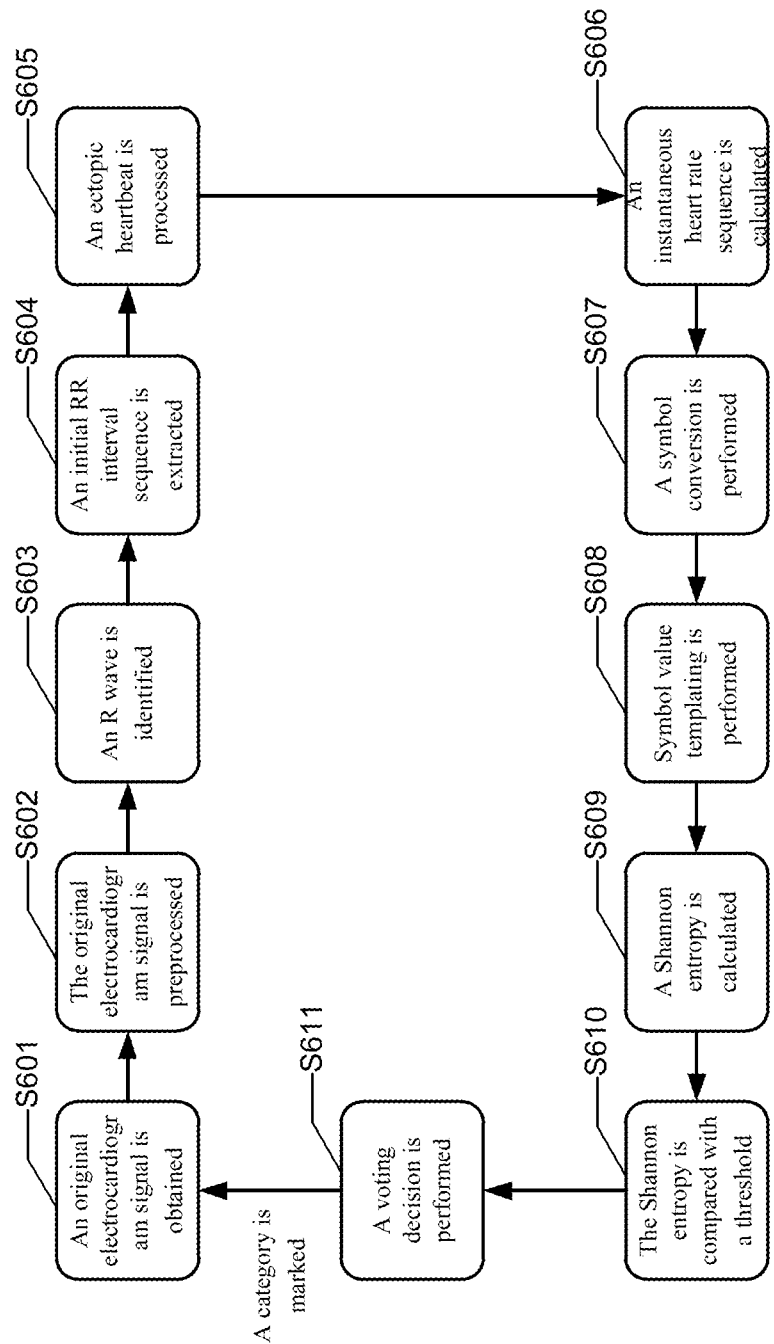
Figure 7:
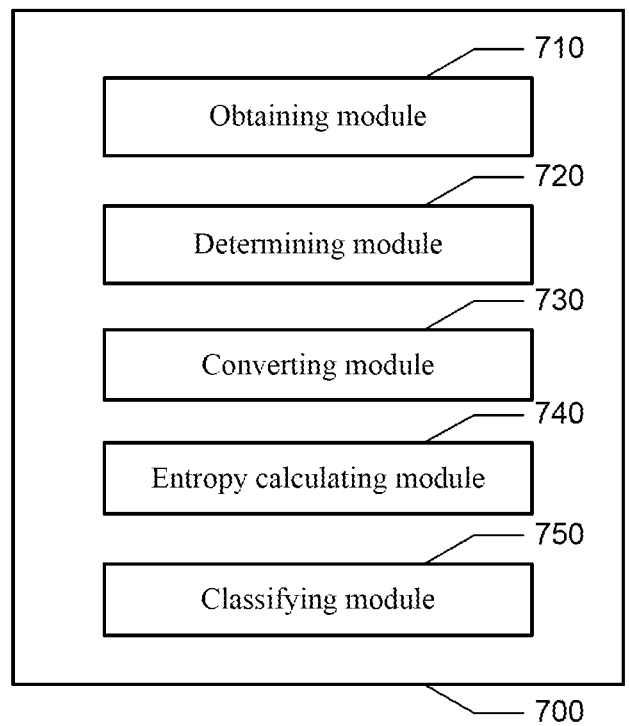
Figure 8:
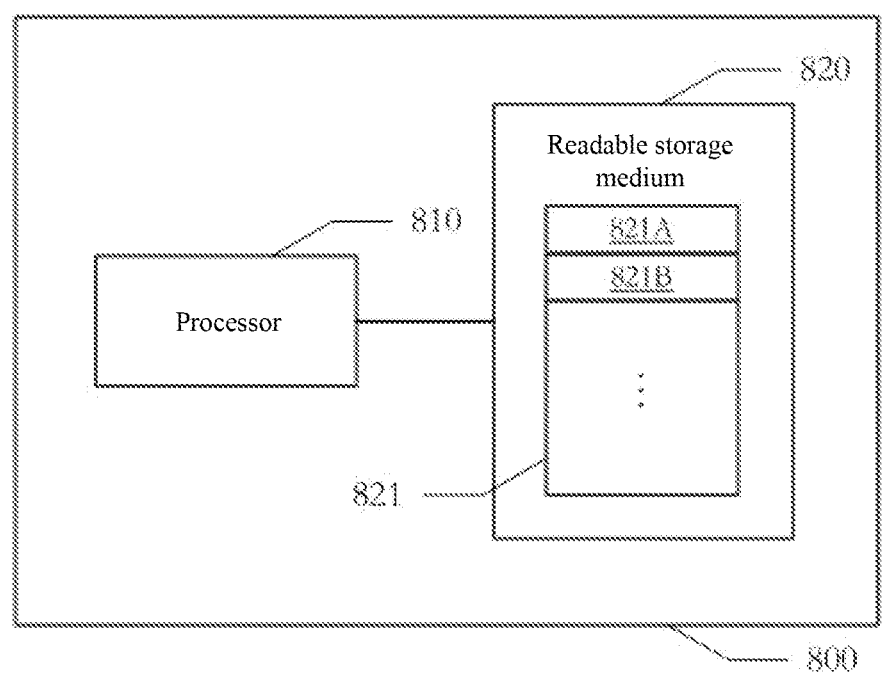

In order to explain the embodiments of the present disclosure or existing technical solutions more clearly, accompanying drawings used in the description of the embodiments may be introduced briefly. It should be noted that the drawings in the following description are only some embodiments of the present disclosure. For those of ordinary skill in the art, other drawings may be obtained based on these drawings without creative work. In the accompanying drawings:

FIG. 1 schematically shows a flowchart of a method for processing an electrocardiogram signal according to some embodiments of the present disclosure;

FIG. 2A schematically shows a flowchart of a method for processing an electrocardiogram signal according to some embodiments of the present disclosure;

FIG. 2B schematically shows a flowchart of a method for processing an electrocardiogram signal according to some embodiments of the present disclosure;

FIG. 3 schematically shows a flowchart of a method for processing an electrocardiogram signal according to some embodiments of the present disclosure;

FIG. 4 schematically shows an exemplary diagram of a process of converting an interval sequence into a symbol value sequence according to some embodiments of the present disclosure;

FIG. 5 schematically shows an exemplary diagram of a voting decision process according to some embodiments of the present disclosure;

FIG. 6A schematically shows an exemplary diagram of a process of processing an electrocardiogram signal according to some embodiments of the present disclosure;

FIG. 6B schematically shows an exemplary diagram of a process of processing an electrocardiogram signal according to some embodiments of the present disclosure;

FIG. 7 schematically shows an apparatus for processing an electrocardiogram signal according to some embodiments of the present disclosure; and FIG. 8 schematically shows a block diagram of an electronic device according to some embodiments of the present disclosure.

DETAILED DESCRIPTION

In order to make the objectives, technical solutions, and advantages of the embodiments of the present disclosure clearer, the technical solutions in the embodiments of the present disclosure may be described clearly and completely in conjunction with the accompanying drawings in the embodiments of the present disclosure. Obviously, the described embodiments are part of the embodiments of the present disclosure, but not all of them. Based on the described embodiments of the present disclosure, all other embodiments obtained by those of ordinary skill in the art without creative labor are within the protection scope of the present disclosure. It should be noted that throughout the drawings, same elements are represented by same or similar reference signs. In the following description, some specific embodiments are only used for descriptive purposes, and should not be construed as limiting the present disclosure, but are merely examples of the embodiments of the present disclosure. In addition, in the following description, descriptions of well-known structures and technologies are omitted to avoid unnecessarily obscuring the concept of the present disclosure.

The terms used herein are only for describing specific embodiments, and are not intended to limit the present disclosure. The terms "comprising", "including", etc. used herein indicate the existence of the described features, steps, operations and/or components, but do not exclude the presence or addition of one or more other features, steps, operations or components.

All terms used herein (including technical and scientific terms) have meanings commonly understood by those skilled in the art, unless otherwise defined. It should be noted that the terms used herein should be interpreted as having meanings consistent with the context of this description, and should not be explained in an idealized or overly rigid manner.

In the case of using an expression similar to "at least one of A, B, C, etc.", it should be generally interpreted according to the meaning of the expression commonly understood by those skilled in the art (for example, "a system having at least one of A, B and C" should include but is not limited to systems having A alone, B alone, C alone, A and B, A and C, B and C, and/or a system having A, B, C, etc.). In the case of using an expression similar to "at least one of A, B, or C, etc.", it should be generally interpreted according to the meaning of the expression commonly understood by those skilled in the art (for example, "a system having at least one of A, B or C" should include but is not limited to systems having A alone, B alone, C alone, A and B, A and C, B and C, and/or a system having A, B, C, etc.).

An electrocardiogram (ECG) signal is a comprehensive reflection of electrical heart activities on a body surface. Accurate classification for an ECG signal may provide effective assistance for scenarios such as clinical monitoring and telemedicine. The ECG signal may be classified by training a classifier. In this manner, a large amount of sample data is prepared, feature construction is performed on the sample data, and the classifier is trained based on the feature of the sample data until an optimization goal is reached. However, this is complicated and less efficient.

According to some embodiments of the present disclosure, a method for processing an electrocardiogram signal is provided, which will be described below. It should be noted that the sequence number of each operation in the following method is only used as an indication of the operation for convenience of description, and should not be regarded as indicating an order of implementing the various operations. It is not necessary to implement the method exactly in the shown order, unless explicitly stated otherwise.

FIG. 1 schematically shows a flowchart of a method for processing an electrocardiogram signal according to some embodiments of the present disclosure.

As shown in FIG. 1, the method may include the following operations S110 to S150.

In operation S110, an electrocardiogram signal is obtained.

The obtained electrocardiogram signal contains a plurality of selected waves. The electrocardiogram signal may include a plurality of electrocardiogram waveforms, such as a P wave, Q wave, R wave, S wave, T wave, etc. The "selected wave" as used herein refers to at least one of the plurality of electrocardiographic waveforms described above.

Then, in operation S120, an interval sequence for the plurality of selected waves in the electrocardiogram signal is determined.

The interval sequence for the plurality of selected waves contains a plurality of time intervals indicating time intervals between the selected waves in the electrocardiogram signal.

Then, in operation S130, the interval sequence is converted into a symbol value sequence, based on symbolic dynamics.

For example, the interval sequence may be converted into a symbol value sequence by symbolic encoding the interval sequence in an amplitude domain based on symbolic dynamics. Thus, the interval sequence is simplified to a symbol value sequence containing finite number of symbol values.

Then, in operation S140, a Shannon entropy of the symbol value sequence is determined.

In information theory, a Shannon entropy is a measure for uncertainty, and is usually used to solve a problem of information quantification. The greater a value of Shannon entropy of an event is, the more information the event carries. The smaller a value of Shannon entropy of an event is, the less information the event carries.

Then, in operation S150, the electrocardiogram signal is classified, based on a value of the Shannon entropy.

Those skilled in the art may understand that according to the method for processing an electrocardiogram signal according to the embodiments of the present disclosure an interval sequence indicating time intervals between selected waves in an electrocardiogram signal is converted into a coarse-grained higher-resolution symbol value sequence, based on symbolic dynamics. A Shannon entropy of the symbol value sequence is calculated. Then the electrocardiogram signal is classified according to a value of the Shannon entropy, in order to obtain a classified result for the electrocardiogram signal. On the one hand, calculation speed may be improved, by symbolizing the interval sequence in an amplitude domain. On the other hand, influence of irrelevant noise may be discarded while preserving essential features of the electrocardiogram signal, by selecting an appropriate coding method. In this manner, uncertainty of the electrocardiogram features may be measured more accurately by the Shannon entropy of the symbol value sequence, thereby obtaining a more accurate classified result. An algorithm for this process is less complex without training a classifier, and is simple and easy to use.

FIG. 2A schematically shows a flowchart of a method for processing an electrocardiogram signal according to some embodiments of the present disclosure. FIG. 2A is used to exemplarily describe the implementation process of operation S120 shown in FIG. 1.

As shown in FIG. 2A, the operation S120 of determining an interval sequence for the plurality of selected waves may include the following sub-operations S121 to S122.

In sub-operation S121, a peak of each of the plurality of selected waves is identified respectively.

For example, in the operation S121, various identification algorithms may be applied to identify a peak of each of the plurality of selected waves respectively based on features of the selected waves. The electrocardiogram signal may be indicated as a distribution of amplitudes of the electrocardiogram signal with respect to time. Therefore, it is possible to determine time points for the plurality of peaks, by identifying a peak of each of the plurality of selected waves respectively.

In sub-operation S122, an interval sequence for the plurality of selected waves is determined, based on time intervals between every two adjacent peaks of the plurality of selected waves.

FIG. 2B schematically shows a flowchart of a method for processing an electrocardiogram signal according to some embodiments of the present disclosure. FIG. 2B is used to exemplarily describe the implementation process of sub-operation S122 shown in FIG. 2A.

As shown in FIG. 2B, an electrocardiogram signal containing M+1 selected waves is taken as an example. The sub-operation S122 of determining the interval sequence, based on time intervals between every two adjacent peaks of the plurality of selected waves may include the following sub-operations S1221 to S1222.

In sub-operation S1221, an initial interval sequence containing M time intervals is determined, based on time intervals between every two adjacent peaks of the M+1 selected waves.

In sub-operation S1222, an interval sequence containing N time intervals is obtained, by preprocessing the initial interval sequence.

M and N are both positive integers, and M is greater than or equal to N.

For example, a QRS wave complex is a typical electrocardiogram waveform in an electrocardiogram signal, reflecting electrical behaviors of a heart in ventricular contraction process. The QRS wave complex contains Q waves, R waves, and S waves. R wave is set as the selected wave in this example. Peaks of M+1 R waves in an electrocardiogram signal are identified. Time intervals between every two adjacent R wave peaks are regarded as RR intervals. The initial interval sequence contains M RR intervals, which may be expressed as: $\{RR_1, RR_2, \ldots, RR_M\}$. Abnormal time intervals in the initial RR interval sequence may be removed, by preprocessing the initial RR interval sequence. An interval sequence may be obtained, which may be expressed as: $\{RR_1, RR_2, \ldots, RR_N\}$. The R wave peak in the electrocardiogram signal may be identified in many ways, such as methods based on an amplitude, a slope, an area, etc., which is not limited here. In this example, a P-T (Pan-Tompkins) algorithm is used to locate the R wave peak in the electrocardiogram signal.

The obtaining an interval sequence containing N time intervals, by preprocessing the initial interval sequence is described according to the following embodiments.

Exemplarily, the obtaining an interval sequence containing N time intervals, by preprocessing the initial interval sequence containing M time intervals may be performed in the following manner.

First, a mean (also called a sequence average) of the M time intervals in the initial interval sequence is determined. On the one hand, for any time interval of the M time intervals, whether the any time interval belongs to a second predetermined category or not is determined, based on a difference between the any time interval and the sequence average. If it is determined that the any time interval belongs to a second predetermined category, the any time interval and a subsequent time interval of the any time interval are deleted from the initial interval sequence.

Additionally or alternatively, for any time interval of the M time intervals, a combined interval is obtained, by summing the any time interval and a subsequent time interval of the any time interval, and whether the any time interval belongs to a second predetermined category or not is determined, based on a difference between the combined interval and the sequence average. If it is determined that the any time interval belongs to a second predetermined category, the any time interval and the subsequent time interval of the any time interval are combined as one time interval. The second predetermined category may, for example, indicate a time interval for ectopic heartbeats.

For example, for the initial interval sequence $\{RR_1, RR_2, \ldots, RR_M\}$, the mean of the M time intervals mean(RR) is determined according to formula (1).

$$\text{mean}(RR) = \frac{\sum_{i=1}^{M} RR_i}{M} \qquad \text{formula (1)}$$

$RR_i$ represents an i-th time interval, and i is an integer not smaller than 1 and not greater than M. If a difference between $RR_i$ and mean(RR) satisfies formula (2), then it is determined that $RR_i$ is too large, and $RR_i$ corresponds to an ectopic heartbeat. Thus, $RR_i$ and $RR_{i+1}$ need to be deleted. If i=M, only $RR_i$ is deleted.

$$\frac{RR_i}{\text{mean}(RR)} > a \qquad \text{formula (2)}$$

In formula (2), a is a preset parameter, which may be adjusted as needed. In principle, the preset parameter should be greater than 1. a=1.8 in this example.

In addition, if a difference between the combined interval $(RR_{i-1}+RR_i)$ and mean(RR) satisfies formula (3) (i.e., compared with $RR_{i-1}$, $(RR_{i-1}+RR_i)$ is closer to mean(RR) and compared with $RR_i$, $(RR_{i-1}+RR_i)$ is closer to mean(RR)), it is determined that both $RR_{i-1}$ and $RR_i$ are too small, and a misidentified heartbeat may be inserted between two normal heartbeats. Thus, the two adjacent RR values (i.e., $RR_{i-1}$ and $RR_i$) are combined as one RR interval.

$$\begin{cases} |(RR_{i-1} + RR_i) - \text{mean}(RR)| < |RR_{i-1} - \text{mean}(RR)| \\ |(RR_{i-1} + RR_i) - \text{mean}(RR)| < |RR_i - \text{mean}(RR)| \end{cases} \qquad \text{formula (3)}$$

In formula (3), i is an integer greater than 1 and smaller than or equal to M.

After the deleting and combining operations, a new interval sequence is determined, which may be expressed as $\{RR_1, RR_2, \ldots, RR_N\}$, in seconds (s). The new interval sequence contains N time intervals (also called N lengths of heartbeat). N is smaller than or equal to M.

In addition, exemplarily, the obtaining an interval sequence containing N time intervals, by preprocessing the initial interval sequence may be performed in the following manner.

On the one hand, for any time interval of the M time intervals, the any time interval and a subsequent time interval of the any time interval are deleted from the initial interval sequence, if the following condition is satisfied. A ratio of the any time interval to a previous time interval of the any time interval is greater than a second value, and a ratio of a subsequent time interval of the any time interval to the any time interval is greater than a third value. On the other hand, for any time interval of the M time intervals, the any time interval and a subsequent time interval of the any time interval are deleted from the initial interval sequence, if the following condition is satisfied. A ratio of the any time interval to a previous time interval of the any time interval being greater than a fourth value, and a ratio of a subsequent time interval of the any time interval to the any time interval is smaller than a fifth value. The second value is smaller than the third value, and the fourth value is greater than the fifth value.

For example, for the time interval $RR_i$ in the initial interval sequence $\{RR_1, RR_2, \ldots, RR_M\}$, if $RR_i$ satisfies formula (4), it is determined that $RR_i$ corresponds to a premature beat belonging to an ectopic heartbeat. Thus, $RR_i$ and $RR_{i+1}$ need to be deleted. If i=M, only $RR_i$ is deleted.

$$\begin{cases} \dfrac{RR_i}{RR_{i-1}} > b \\ \dfrac{RR_{i+1}}{RR_i} > c \end{cases} \qquad \text{formula (4)}$$

In formula (4), i is an integer greater than 1 and smaller than M. b is the second value, c is the third value, and b is smaller than c. b and c may be set as needed. In this example, b=0.9 and c=1.6.

In addition, if $RR_i$ satisfies formula (5), it is determined that $RR_i$ corresponds to an escape beat (also belonging to an ectopic heartbeat) Thus, $RR_i$ and $RR_{i+1}$ need to be deleted. If i=M, only $RR_i$ is deleted.

$$\begin{cases} \dfrac{RR_i}{RR_{i-1}} > d \\ \dfrac{RR_{i+1}}{RR_i} < e \end{cases} \qquad \text{formula (5)}$$

In formula (5), i is an integer greater than 1 and smaller than M. d is the fourth value, e is the fifth value, and d is greater than e. d and e may be set as needed. In this example, d=1.3 and e=0.6.

After deleting ectopic heartbeats, a new interval sequence is determined, which may be expressed as $\{RR_1, RR_2, \ldots, RR_N\}$, in seconds. The new interval sequence contains N time intervals (also called N lengths of heartbeat), and N≤M.

It may be understood that after the preprocessing in the above embodiments, the obtained interval sequence eliminates interference of the ectopic heartbeat on electrocardiogram signal classification. Thus, accuracy of a subsequent classification may be improved effectively. It should be noted that after determining that $RR_i$ corresponds to an ectopic heartbeat, $RR_{i+1}$ is usually influenced by $RR_i$ and may be different from normal length of a heartbeat. For example, $RR_{i+1}$ is a compensatory pause. Therefore, $RR_{i+1}$ may be deleted together with $RR_i$.

FIG. 3 schematically shows a flowchart of a method for processing an electrocardiogram signal according to some embodiments of the present disclosure. FIG. 3 is used to exemplarily describe the implementation process of operation S130 shown in FIG. 1.

As shown in FIG. 3, the operation S130 of converting the interval sequence into a symbol value sequence, based on symbolic dynamics may include the following sub-operations S131 to S133.

In sub-operation S131, an instantaneous heart rate sequence is obtained, by calculating an instantaneous heart rate for each time interval in the interval sequence.

Then, in sub-operation S132, a plurality of encoded symbols are obtained, by performing a first encoding on each of a plurality of instantaneous heart rates in the instantaneous heart rate sequence respectively; and a symbol sequence is determined based on the plurality of encoded symbols.

Next, in sub-operation S133, a plurality of symbol values is obtained, by performing a second encoding on each of the plurality of encoded symbols in the symbol sequence respectively; and a symbol value sequence is determined, based on the plurality of symbol values.

For example, for the interval sequence $\{RR_1, RR_2, \ldots, RR_N\}$, an instantaneous heart rate for the time interval RR is calculated by $HR_i = 60/RR_i$, in bpm (beats per minute). The instantaneous heart rate indicates a number of heartbeats per minute. i is an integer not smaller than 1 and not greater than N. Thus, an instantaneous heart rate sequence $\{HR_1, HR_2, \ldots, HR_N\}$ is obtained.

Exemplarily, the obtaining a plurality of encoded symbols, by performing a first encoding on each of a plurality of instantaneous heart rates in the instantaneous heart rate sequence respectivelymay be performed in a following manner.

For any instantaneous heart rate of the instantaneous heart rates in the instantaneous heart rate sequence, the any instantaneous heart rate is classifyed, based on a value of the any instantaneous heart rate. If the any instantaneous heart rate belongs to a first class, a predetermined symbol is set as an encoded symbol for the any instantaneous heart rate. If the any instantaneous heart rate belongs to a second class, a ratio of the any instantaneous heart rate to a first value is set as an encoded symbol for the any instantaneous heart rate.

For example, the classifying the any instantaneous heart rate, based on a value of the any instantaneous heart rate may be implemented in a following manner. If the value of the any instantaneous heart rate is greater than or equal to a predetermined value, it is determined that the instantaneous heart rate belongs to the first class. If the value of the instantaneous heart rate is smaller than the predetermined value, it is determined that the instantaneous heart rate belongs to the second class. The first encoding may be performed on a instantaneous heart rate $HR_i$ in the instantaneous heart rate sequence $\{HR_1, HR_2, \ldots, HR_N\}$ according to formula (6), in order to obtain a encoded symbol $SY_i$ for $HR_i$. In this example, the encoded symbol $SY_i$ is represented by two digits.

$$SY_i = \begin{cases} \dfrac{f}{g}, & HR_i \geq f \\ \left[\dfrac{HR_i}{g}\right], & HR_i < f \end{cases} \qquad \text{formula (6)}$$

f is the predetermined value for classifying each instantaneous heart rate, g is the first value, and the ratio of the predetermined value to the first value is the predetermined symbol in this example. The parameters may be set as needed. In this example, f=315, g=5, and the predetermined symbol is 63. [ ] means rounding operation, and $0 \le SY_i \le 63$. After the first encoding process, the instantaneous heart rate sequence $\{HR_1, HR_2, \ldots, HR_N\}$ is converted into a symbol sequence $\{SY_1, SY_2, \ldots, SY_N\}$.

Exemplarily, the obtaining a plurality of symbol values, by performing a second encoding on each of the plurality of encoded symbols in the symbol sequence respectively may be performed in a following manner. For any encoded symbol of the encoded symbols in the symbol sequence, a weighted sum of the any encoded symbol, a previous encoded symbol of the any encoded symbol and a subsequent encoded symbol of the any encoded symbol is calculated; and the weighted sum is set as a symbol value for the any encoded symbol.

For example, the second encoding may be performed on an encoded symbol $SY_i$ in the symbol sequence $\{SY_1, SY_2, \ldots, SY_N\}$ according to formula (7), in order to obtain a symbol value $SYV_i$ for the encoding symbol $SY_i$. The second encoding process may be called a symbol value templating process as well.

$$SYV_i = SY_{i-1} \times h_1 + SY_i \times h_2 + SY_{i+1} \times h_3 \quad \text{formula (7)}$$

In formula (7), i is an integer greater than 0 and smaller than N. $h_1$ represents the first weight, $h_2$ represents the second weight, and $h_3$ represents the third weight. $h_1$, $h_2$, and $h_3$ may be set as needed. In this example, $h_1=2^{12}$, $h_2=2^6$, and $h_3=1$. For example, for a symbol sequence $\{01, 20, 13\}$, a symbol value for the encoded symbol "20" equals to $01 \times 4096 + 20 \times 64 + 13$, and $0 \le SYV_i \le 262143$. After the second encoding process, the symbol sequence $\{SY_1, SY_2, \ldots, SY_N\}$ is converted into a symbol value sequence $\{SYV_1, SYV_2, \ldots, SYV_N\}$.

FIG. 4 schematically shows an exemplary diagram of a process of converting an interval sequence into a symbol value sequence according to some embodiments of the present disclosure.

As shown in FIG. 4, 4-1 is a schematic diagram of an interval sequence, showing amplitude changes from the 1st time interval to the 61st time interval. 4-2 is a schematic diagram of an instantaneous heart rate sequence, showing amplitude changes from the 1st instantaneous heart rate to the 61st instantaneous heart rate. 4-3 is a schematic diagram of a symbol sequence, showing amplitude changes from the 1st encoded symbol to the 61st encoded symbol. 4-4 is a schematic diagram of a symbol value sequence, showing amplitude changes from the 2nd symbol value to the 60th symbol value.

According to the converting the interval sequence to the symbol value sequence shown in FIG. 4, the time interval has a continuous range, while the symbol value has a finite range. Irrelevant detailed information is intended to be removed, and data is classified base on discrete values. Thus, time interval data having many possibilities is converted into a finite number of symbol values. In this manner, the electrocardiogram signal is maintained large-scale, and influence of irrelevant noise may be discarded, which is beneficial to a subsequent classification for the electrocardiogram signal based on a Shannon entropy of the symbol value sequence.

According to some embodiments of the present disclosure, the determining a Shannon entropy of the symbol value sequence may be implemented in a following manner.

A plurality of symbol value sections is preset. Then, for any symbol value section of the plurality of symbol value sections, a ratio of a number of symbol values in the symbol value sequence falling within the any symbol value section to a number of symbol values in the symbol value sequence is calculated, and the ratio is set as a distribution probability of the symbol value sequence with respect to the any symbol value section. Next, the Shannon entropy of the symbol value sequence is determined, based on the distribution probability of the symbol value sequence with respect to each of the plurality of symbol value sections.

For example, based on the formula (7), a minimum value of the symbol value is 0, and a maximum value of the symbol value is 262143. A value space [0, 262143] is called a symbol value space (SYV space). The SYV space may be divided into 128 symbol value sections by 2048, the 128 symbol value sections are regarded as 128 preset symbol value sections. For example, the first symbol value section is [0, 2047], the second symbol value section is [2048, 4095], etc. Alternatively, in another example, for the SYV space [0, 262143], the SYV space may be divided into 64 symbol value sections by 4096, the 64 symbol value sections are regarded as 64 preset symbol value sections. Different numbers of symbol value sections may be preset, according to different symbol value spaces and different division intervals, which is not limited here.

For example, Q symbol value sections are preset. A number of symbol values in the symbol value sequence $\{SYV_1, SYV_2, \ldots, SYV_N\}$ falling within the j-th symbol value section is $n_j$, and a total number of symbol values in the symbol value sequence $\{SYV_1, SYV_2, \ldots, SYV_N\}$ is N. A ratio $p_j$ equals to $n_j/N$, and $p_j$ is regarded as a distribution probability of the symbol value sequence with respect to the j-th symbol value section. j is an integer not smaller than 1 and not greater than Q, and $n_j \le N$. Then, a Shannon entropy of the symbol value sequence $\{SYV_1, SYV_2, \ldots, SYV_N\}$ may be determined, based on a distribution probability of the symbol value sequence $\{SYV_1, SYV_2, \ldots, SYV_N\}$ with respect to each of the preset Q symbol value sections.

According to the embodiments of the present disclosure, a definition for the Shannon entropy is revised, in order to more accurately adapt to the classification for the electrocardiogram signal. Exemplarily, the determining the Shannon entropy of the symbol value sequence, based on the distribution probability of the symbol value sequence with respect to each of the plurality of symbol value sections may be implemented in a following manner.

On the one hand, a distribution expectation of the symbol value sequence with respect to the plurality of symbol value sections is calculated, based on the distribution probability of the symbol value sequence with respect to each of the plurality of symbol value sections. On the other hand, a gain coefficient is determined, based on the number of symbol values in the symbol value sequence and a number of the plurality of symbol value sections. Then, the Shannon entropy of the symbol value sequence is determined, based on the distribution expectation and the gain coefficient.

Referring to the above example, the number of symbol value sections is Q, and the distribution probability of the symbol value sequence $\{SYV_1, SYV_2, \ldots, SYV_N\}$ with respect to the j-th symbol value section is $p_j$. The Shannon entropy SE of the symbol value sequence $\{SYV_1, SYV_2, \ldots, SYV_N\}$ may be calculated according to formula (8).

$$SE = -\frac{N}{Q \times \log_2 Q} \sum_{i=1}^{Q} p_i \times \log_2 p_i \quad \text{formula (8)}$$

$$\frac{N}{Q \times \log_2 Q}$$

is the gain coefficient, and $-\Sigma_{i=1}^{Q} p_i \times \log_2 p_i$ is the distribution expectation of the symbol value sequence $\{SYV_1, SYV_2, \ldots, SYV_N\}$ with respect to the Q symbol value sections.

According to some embodiments of the present disclosure, after the Shannon entropy of the symbol value sequence is calculated, a category of the electrocardiogram signal may be determined by comparing the value of the Shannon entropy with a first predetermined threshold ThSe.

Exemplarily, the the classifying the electrocardiogram signal, based on a value of the Shannon entropy may include the following operation. If the value of the Shannon entropy is greater than a first predetermined threshold, it is determined that the electrocardiogram signal belongs to a first predetermined category. For the electrocardiogram signal, if the Shannon entropy of the symbol value sequence for the electrocardiogram signal is small, fluctuation of the electrocardiogram signal is relatively stable. The larger the Shannon entropy of the symbol value sequence for the electrocardiogram signal is, the less stable the fluctuation of the electrocardiogram signal is. An unstable electrocardiogram fluctuation is usually caused by some diseases. In this embodiment, the first predetermined threshold (also called Shannon entropy threshold) is used as a boundary, in order to determine whether the electrocardiogram signal belongs to the first predetermined category or not. Exemplarily, the first predetermined category may be related to a certain disease. For example, the first predetermined category may be related to atrial fibrillation (AF).

The setting of a length N of the symbol value sequence and the Shannon entropy threshold ThSe may directly affect accuracy of a classification result. If the Shannon entropy threshold is too small, some normal electrocardiogram signals may be classified into the first predetermined category. If the Shannon entropy is too high, it may lead to insensitivity to some abnormal electrocardiogram signals. Improper selection of the length of the symbol value sequence may lead to inaccurate classification results. If the symbol value sequence is too long, the real-time performance and complexity of the algorithm may also be affected. After parameter tuning, for example, the Shannon entropy threshold ThSe may be set between 0.2 and 0.5, and the length N of the symbol value sequence may be set between 15 and 60. Based on these settings, both sensitivity and accuracy may be ensured. In addition, it is possible to classify the electrocardiogram signal by only using signal data within about one minute, so that a relationship between the electrocardiogram signal and a certain disease (such as atrial fibrillation) may be acknowledged. Therefore, assistance for scenarios such as clinical monitoring and telemedicine may be provided.

Further, after determining that the obtained electrocardiogram signal belongs to the first predetermined category, the following voting decision mechanism may be used to more accurately locate a position of the heartbeat in the electrocardiogram signal belonging to the first predetermined category.

Exemplarily, the method for processing an electrocardiogram signal according to the embodiments of the present disclosure may further include the following manners.

First, a sliding window is set. A length of the sliding window is smaller than a length of the symbol value sequence. A plurality of symbol value subsequences is extracted from the symbol value sequence, by sliding the sliding window from a head of the symbol value sequence to a tail of the symbol value sequence. A step of the sliding window is one symbol value. Then, for any symbol value subsequence of the plurality of symbol value subsequences, a Shannon entropy of the any symbol value subsequence is determined. If the Shannon entropy of the any symbol value subsequence is greater than a first predetermined threshold, a predetermined point to a score of each symbol value in the any symbol value subsequence is added. The predetermined point may be set as needed, which is not limited here. Then, a total score of each symbol value in the symbol value sequence is determined, after completing the sliding of the sliding window; and it is determined that a symbol value having a total score greater than a second predetermined threshold belongs to a first predetermined category.

FIG. 5 schematically shows an exemplary diagram of a voting decision process according to some embodiments of the present disclosure.

As shown in FIG. 5, a length of a sliding window is 20 in this example, corresponding to a length of 20 symbol values. A length N of the symbol value sequence $\{SYV_1, SYV_2, \ldots, SYV_N\}$ is greater than 20. The sliding window is slid a head of the symbol value sequence to a tail of the symbol value sequence, in order to extract a plurality of symbol value subsequences. For example, the first symbol value subsequence is $\{SYV_1, SYV_2, \ldots, SYV_{20}\}$, the second symbol value subsequence is $\{SYV_2, SYV_3, \ldots, SYV_{21}\}$, and the third symbol value subsequence is $\{SYV_3, SYV_4, \ldots, SYV_{22}\}$, etc.

A Shannon entropy of each extracted symbol value subsequence is calculated respectively, and the calculating method has a same principle as calculating the Shannon entropy of the symbol value sequence above, which has been described in details and will not be repeated here. For example, the predetermined score is 1. For example, the Shannon entropy of the first symbol value subsequence $\{SYV_1, SYV_2, \ldots, SYV_{20}\}$ is calculated as $SE_1$. If $SE_1$ is greater than the first predetermined threshold ThSe, one point is added to a score of each symbol value in the symbol value subsequence $\{SYV_1, SYV_2, \ldots, SYV_{20}\}$. The score of the symbol value $SYV_i$ is expressed as $AF_i$. If $SE_1$ is smaller than or equal to the first predetermined threshold ThSe, the score of each symbol value in the symbol value subsequence $\{SYV_1, SYV_2, \ldots, SYV_{20}\}$ remains unchanged. After calculating the Shannon entropy of all symbol value subsequences and scoring the Shannon entropies, a total score of each symbol value in the symbol value sequence $\{SYV_1, SYV_2, \ldots, SYV_N\}$ may be obtained. If a total score of a symbol value is greater than the second predetermined threshold, it is determined that the symbol value belongs to the first predetermined category. Thus, a heartbeat for the symbol value belongs to the first predetermined category. For example, the heartbeat is related to atrial fibrillation. In this example, the second predetermined threshold is set as 12. In other examples, the second predetermined threshold may be set as needed. In principle, the second predetermined threshold should be smaller than or equal to the length of the sliding window.

Those skilled in the art may understand that the method for processing an electrocardiogram signal according to the embodiments of the present disclosure may classify the electrocardiogram signal. The heartbeat in the electrocardiogram signal belonging to the first predetermined category may be located more accurately, by using the voting decision mechanism. This may have positive impact in the fields of medical diagnosis and monitoring.

In some cases, due to human body movement and contact between the human body and the outside, the electrocardiogram signal may be interfered by noise. This may bring difficulties in processing the electrocardiogram signal. For example, baseline wander may be caused by low-frequency interference such as breathing and electrode movement of a measured object. The baseline wander may cause an electrocardiogram signal to deviate from a normal baseline position in an actual measurement, and slow fluctuations up and down may occur. The electrocardiogram signal contains rich low-frequency components, and the baseline wander may conceal useful information and affect the accuracy of analysis, recognition, classification, and positioning of the electrocardiogram signal.

According to some embodiments of the present disclosure, after the electrocardiogram signal is obtained, the baseline wander noise of the electrocardiogram signal may be removed. Various methods may be applied to remove the baseline wander noise, such as adaptive filtering, Kalman filtering, wavelet transform, etc., which is not limited here. In this example, median filtering is used to suppress the baseline wander efficiently and effectively.

According to the embodiments of the present disclosure, the electrocardiogram signal may be a single-lead electrocardiogram signal, so that a classification result indicating whether a heartbeat is abnormal or not may be obtained. Without processing based on a complex signal in a multi-lead electrocardiogram signal, the method is simple and reliable.

FIG. 6A schematically shows an exemplary diagram of a process of processing an electrocardiogram signal according to some embodiments of the present disclosure. FIG. 6B schematically shows an exemplary diagram of a process of processing an electrocardiogram signal according to some embodiments of the present disclosure. It should be noted that processed shown in FIG. 6A and FIG. 6B are only examples for facilitating the understanding of the present disclosure, which is not limited by the present disclosure.

As shown in FIG. 6A and FIG. 6B, the process may include operations S601 to S610.

In operation S601, an original electrocardiogram signal is obtained.

In operation S602, the original electrocardiogram signal is preprocessed, in order to remove baseline wander noise; and a preprocessed electrocardiogram signal is obtained.

In operation S603, an R wave in the electrocardiogram signal is identified.

In operation S604, an initial RR interval sequence is extracted.

In operation S605, an ectopic heartbeat in the initial RR interval sequence is processed, in order to obtain an RR interval sequence.

In operation S606, an instantaneous heart rate sequence is calculated.

In operation S607, a symbol conversion performed, in order to obtain a symbol sequence.

In operation S608, symbol value templating is performed, in order to obtain a symbol value sequence.

In operation S609, a Shannon entropy of the symbol value sequence is calculated.

In operation S610, the Shannon entropy is compared with a first predetermined threshold, so that a category of the electrocardiogram signal is determined according to a result of the comparison, and the electrocardiogram signal is marked. For example, a first predetermined category is related to atrial fibrillation, such that an electrocardiogram signal belonging to the first predetermined threshold may be marked as "atrial fibrillation related". Then operation S601 is repeated until all electrocardiogram signals are marked.

As shown in FIG. 6B, after operation S610, the process may further include operation S611. In operation S611, an abnormal heartbeat is located within the electrocardiogram signal belonging to the first predetermined category by performing a voting decision, so that the electrocardiogram signal is marked more specifically. For example, one or more heartbeat positions within the electrocardiogram signal belonging to the first predetermined category may be marked as "atrial fibrillation related". The voting decision process has been described in details above, which will not be repeated here. Then operation S601 is repeated until all electrocardiogram signals are marked.

It may be understood that according to the embodiments of the present disclosure, symbolic dynamics and custom Shannon entropy are combined in the process of processing an electrocardiogram signal. The process is more sensitive to electrocardiogram features related to certain diseases, and the algorithm is less complex. Without training a classifier, accuracy and real-time performance of classifying an electrocardiogram signal and positioning an abnormal heartbeat within the electrocardiogram signal may be effectively improved in an electrocardiogram signal monitoring process.

FIG. 7 schematically shows an apparatus for processing an electrocardiogram signal according to some embodiments of the present disclosure.

As shown in FIG. 7, the apparatus 700 for processing an electrocardiogram signal may include an obtaining module 710, a determining module 720, a converting module 730, an entropy calculating module 740, and a classifying module 750.

The obtaining module 710 is configured to obtain an electrocardiogram signal containing a plurality of selected waves.

The determining module 720 is configured to determine an interval sequence for the plurality of selected waves.

The converting module 730 is configured to convert the interval sequence into a symbol value sequence, based on symbolic dynamics.

The entropy calculating module 740 is configured to determine a Shannon entropy of the symbol value sequence.

The classifying module 750 is configured to classify the electrocardiogram signal, based on a value of the Shannon entropy.

It should be noted that the implementation, solved technical problems, achieved functions, and technical effects of the modules/units/subunits, etc. achieved in the above embodiments of the apparatus are respectively same as or similar to the implementation, solved technical problems, achieved functions, and technical effects of the corresponding operations in the embodiments of the method, and will not be repeated here.

Any multiple of the modules, sub modules, units and sub units according to the embodiments of the present disclosure, or at least part of the functions of any number of them may be implemented in one module. Any one or more of the modules, sub modules, units and sub units according to the embodiments of the present disclosure may be split into multiple modules for implementation. Any one or more of the modules, sub modules, units and sub units according to the embodiments of the present disclosure may be implemented at least partially as a hardware circuit, such as a field programmable gate array (FPGA), a programmable logic array (PLA), a system on a chip, a system on a substrate, a system on a package, an Application Specific Integrated Circuit (ASIC), or may be implemented by hardware or firmware in any other reasonable way that integrates or encapsulates the circuit, or may be implemented by any one of the three implementation modes of software, hardware and firmware or an appropriate combination thereof. Alternatively, one or more of the modules, sub modules, units and sub units according to the embodiments of the present disclosure may be at least partially implemented as a computer program module that, when executed, performs the corresponding functions.

FIG. 8 schematically shows a block diagram of an electronic device according to some embodiments of the present disclosure. The electronic device shown in FIG. 8 is only an example, and should not bring any limitation to the function and scope of use of the embodiments of the present disclosure.

As shown in FIG. 8, the electronic device 800 includes one or more processors 810 and a computer-readable storage medium 820. The electronic device 800 may implement the method according to the embodiments of the present disclosure.

For example, the processor 810 may include, for example, a general-purpose microprocessor, an instruction set processor, and/or a related chipset, and/or a special-purpose microprocessor (for example, an application specific integrated circuit (ASIC)), etc. The processor 810 may further include an onboard memory for caching purposes. The processor 810 may be a single processing unit or multiple processing units for executing different actions of the method flow according to the embodiments of the present disclosure.

The computer-readable storage medium 820, for example, may be a non-volatile computer-readable storage medium, include but not limited to: a magnetic storage device (such as magnetic tape or hard disk (HDD)), an optical storage device (such as optical disk (CD-ROM)), a memory (such as random access memory (RAM) or a flash memory, etc.

The computer-readable storage medium 820 may include a computer program 821, and the computer program 821 may include codes/computer-executable instructions. The codes/computer-executable instructions, when executed by the processor 810, cause the processor 810 to implement the method according to the embodiments of the present disclosure or any modification thereof.

The computer program 821 may be configured to have, for example, computer program codes including computer program modules. For example, in some embodiments, the codes in the computer program 821 may include one or more program modules, such as module 821A, module 821B, . . . . It should be noted that the dividing method and number of modules are not fixed. Those skilled in the art may use appropriate program modules or combinations thereof according to the actual situations. The program modules or combinations, when executed by the processor 810, cause the processor 810 to implement the method according to the embodiments of the present disclosure or any modification thereof.

According to the present disclosure, there is further provided a computer-readable storage medium. The computer-readable storage medium may be included in the device/apparatus/system described in the above embodiments, or the computer-readable storage medium may be a single medium without being assembled into the device/apparatus/system. The computer-readable storage medium carries one or more programs, and the one or more programs, when executed, implement the method according to the embodiments of the present disclosure.

According to some embodiments of the present disclosure, the computer-readable storage medium may be a non-volatile computer-readable storage medium, include but not limited to: a portable computer disk, a hard disk, a random access memory (RAM), a read-only memory (ROM), an erasable programmable read-only memory (EPROM or flash memory), a portable compact disk read-only memory (CD-ROM), an optical storage component, a magnetic storage component, or any suitable combination thereof. In the present disclosure, the computer-readable storage medium may be any tangible medium containing or storing a program, and the program may be used by or in combination with an instruction execution system, apparatus, or device.

Although the present disclosure has been shown and described with reference to specific exemplary embodiments of the present disclosure, those skilled in the art should understand that various changes in form and in detail may be made to the present disclosure without departing from the spirit and scope of the present disclosure defined by the appended claims and equivalents thereof. Therefore, the scope of the present disclosure should not be limited to the above embodiments, but should be defined by the appended claims and equivalents thereof.

I claim:

1. A method for processing an electrocardiogram signal, comprising:
   obtaining an electrocardiogram signal containing a plurality of selected waves;
   determining an interval sequence for the plurality of selected waves;
   converting the interval sequence into a symbol value sequence, based on symbolic dynamics;
   determining a Shannon entropy of the symbol value sequence; and
   classifying the electrocardiogram signal, based on a value of the Shannon entropy;
   wherein the classifying the electrocardiogram signal, based on a value of the Shannon entropy comprises: determining that the electrocardiogram signal belongs to a first predetermined category, in response to the value of the Shannon entropy being greater than a first predetermined threshold.

2. The method of claim 1, wherein the converting the interval sequence into a symbol value sequence, based on symbolic dynamics comprises:
   obtaining an instantaneous heart rate sequence, by calculating an instantaneous heart rate for each time interval in the interval sequence;
   obtaining a plurality of encoded symbols, by performing a first encoding on each of a plurality of instantaneous heart rates in the instantaneous heart rate sequence respectively;
   determining a symbol sequence based on the plurality of encoded symbols;
   obtaining a plurality of symbol values, by performing a second encoding on each of the plurality of encoded symbols in the symbol sequence respectively; and
   determining a symbol value sequence, based on the plurality of symbol values.

3. The method of claim 2, wherein the obtaining a plurality of encoded symbols, by performing a first encoding on each of a plurality of instantaneous heart rates in the instantaneous heart rate sequence respectively comprises:
for any instantaneous heart rate of the instantaneous heart rates in the instantaneous heart rate sequence,
classifying the any instantaneous heart rate, based on a value of the any instantaneous heart rate;
setting a predetermined symbol as an encoded symbol for the any instantaneous heart rate, in response to the any instantaneous heart rate belonging to a first class; and
setting a ratio of the any instantaneous heart rate to a first value as the encoded symbol for the any instantaneous heart rate, in response to the any instantaneous heart rate belonging to a second class.

4. The method of claim 2, wherein the obtaining a plurality of symbol values, by performing a second encoding on each of the plurality of encoded symbols in the symbol sequence respectively comprises:
for any encoded symbol of the encoded symbols in the symbol sequence,
calculating a weighted sum of the any encoded symbol, a previous encoded symbol of the any encoded symbol and a subsequent encoded symbol of the any encoded symbol; and
setting the weighted sum as a symbol value for the any encoded symbol.

5. The method of claim 1, wherein the determining a Shannon entropy of the symbol value sequence comprises:
presetting a plurality of symbol value sections;
for any symbol value section of the plurality of symbol value sections, calculating a ratio of a number of symbol values in the symbol value sequence falling within the any symbol value section to a number of symbol values in the symbol value sequence, and setting the ratio as a distribution probability of the symbol value sequence with respect to the any symbol value section; and
determining the Shannon entropy of the symbol value sequence, based on the distribution probability of the symbol value sequence with respect to each of the plurality of symbol value sections.

6. The method of claim 5, wherein the determining the Shannon entropy of the symbol value sequence, based on the distribution probability of the symbol value sequence with respect to each of the plurality of symbol value sections comprises:
calculating a distribution expectation of the symbol value sequence with respect to the plurality of symbol value sections, based on the distribution probability of the symbol value sequence with respect to each of the plurality of symbol value sections;
determining a gain coefficient, based on the number of symbol values in the symbol value sequence and a number of the plurality of symbol value sections; and
determining the Shannon entropy of the symbol value sequence, based on the distribution expectation and the gain coefficient.

7. The method of claim 1, further comprising:
setting a sliding window, wherein a length of the sliding window is smaller than a length of the symbol value sequence;
extracting a plurality of symbol value subsequences from the symbol value sequence, by sliding the sliding window from a head of the symbol value sequence to a tail of the symbol value sequence, wherein a step of the sliding window is one symbol value;
for any symbol value subsequence of the plurality of symbol value subsequences, determining a Shannon entropy of the any symbol value subsequence, and adding one point to a score of each symbol value in the any symbol value subsequence, in response to the Shannon entropy of the any symbol value subsequence being greater than a first predetermined threshold;
determining a total score of each symbol value in the symbol value sequence, after completing the sliding of the sliding window; and
determining that a symbol value having the total score greater than a second predetermined threshold belongs to a first predetermined category.

8. The method of claim 1, wherein the determining an interval sequence for the plurality of selected waves comprises:
identifying a peak of each of the plurality of selected waves respectively; and
determining the interval sequence, based on time intervals between every two adjacent peaks of the plurality of selected waves.

9. The method of claim 8, wherein the electrocardiogram signal contains M+1 selected waves;
the determining the interval sequence, based on time intervals between every two adjacent peaks of the plurality of selected waves comprises:
determining an initial interval sequence containing M time intervals, based on time intervals between every two adjacent peaks of the M+1 selected waves; and
obtaining an interval sequence containing N time intervals, by preprocessing the initial interval sequence, wherein M and N are both positive integers, and M is greater than or equal to N.

10. The method of claim 9, wherein the obtaining an interval sequence containing N time intervals, by preprocessing the initial interval sequence comprises:
determining a mean of the M time intervals;
for any time interval of the M time intervals, determining whether the any time interval belongs to a second predetermined category or not, based on a difference between the any time interval and the mean of M time intervals; and
deleting the any time interval and a subsequent time interval of the any time interval from the initial interval sequence, in response to determining that the any time interval belongs to the second predetermined category.

11. The method of claim 9, wherein the obtaining an interval sequence containing N time intervals, by preprocessing the initial interval sequence comprises:
determining a mean of the M time intervals;
for any time interval of the M time intervals, obtaining a combined interval, by summing the any time interval and a subsequent time interval of the any time interval;
determining whether the any time interval belongs to a second predetermined category or not, based on a difference between the combined interval and the mean of M time intervals; and
combining the any time interval and the subsequent time interval of the any time interval as one time interval, in response to determining that the any time interval belongs to the second predetermined category.

12. The method of claim 9, wherein the obtaining an interval sequence containing N time intervals, by preprocessing the initial interval sequence comprises at least one of for any time interval of the M time intervals, deleting the any time interval and a subsequent time interval of the any time interval from the initial interval sequence, in response to a ratio of the any time interval to a previous time interval of the any time interval being greater than a second value, and a ratio of the subsequent time interval of the any time interval to the any time interval being greater than a third value; and for the any time interval, deleting the any time interval and the subsequent time interval of the any time interval from the initial interval sequence, in response to the ratio of the any time interval to the previous time interval of the any time interval being greater than a fourth value, and the ratio of the subsequent time interval of the any time interval to the any time interval being smaller than a fifth value, wherein the second value is smaller than the third value, and the fourth value is greater than the fifth value.

13. The method of claim 1, further comprising:

removing baseline wander noise of the electrocardiogram signal, after obtaining the electrocardiogram signal.

14. The method of claim 1, wherein the electrocardiogram signal is a single-lead electrocardiogram signal.

15. An electronic device, comprising:
a memory, configured to store instructions; and
at least one processor, configured to execute the instructions stored in the memory, in order to implement the method of claim 1.

16. A non-transitory computer storage medium storing computer readable instructions thereon, the computer readable instructions, when executed by a computer, implement the method of claim 1.

* * * * *